(12) United States Patent
Maurer

(10) Patent No.: US 9,095,817 B2
(45) Date of Patent: Aug. 4, 2015

(54) DEVICE FOR THE TREATMENT OF BIOLOGICAL FLUID

(75) Inventor: Andreas Maurer, Tubingen (DE)

(73) Assignee: NOVALUNG GMBH, Talheim (DE)

( * ) Notice: Subject to any disclaimer, the term of this patent is extended or adjusted under 35 U.S.C. 154(b) by 0 days.

(21) Appl. No.: 13/148,476

(22) PCT Filed: Feb. 11, 2010

(86) PCT No.: PCT/EP2010/000852
§ 371 (c)(1),
(2), (4) Date: Dec. 13, 2011

(87) PCT Pub. No.: WO2010/091867
PCT Pub. Date: Aug. 19, 2010

(65) Prior Publication Data
US 2012/0190103 A1   Jul. 26, 2012

(30) Foreign Application Priority Data

Feb. 12, 2009   (DE) .......................... 10 2009 008 601

(51) Int. Cl.
*C12M 1/00* (2006.01)
*C12M 3/00* (2006.01)
*C12M 1/34* (2006.01)
(Continued)

(52) U.S. Cl.
CPC .............. *B01D 63/026* (2013.01); *A61M 1/16* (2013.01); *A61M 1/1698* (2013.01); *A61M 1/34* (2013.01); *B01D 63/043* (2013.01); *B01D 2317/08* (2013.01); *B01D 2319/06* (2013.01)

(58) Field of Classification Search
USPC .......................................... 435/283.1–309.4
See application file for complete search history.

(56) References Cited

U.S. PATENT DOCUMENTS

| 3,834,544 A | 9/1974 | Tyson, Jr. et al. |
| 3,969,240 A | 7/1976 | Kolobow et al. |

(Continued)

FOREIGN PATENT DOCUMENTS

| DE | 3207174 A1 | 9/1983 |
| DE | 3923692 A1 | 1/1991 |

(Continued)

*Primary Examiner* — Nathan Bowers
*Assistant Examiner* — Lydia Edwards
(74) *Attorney, Agent, or Firm* — Sam K. Tahmassebi; TechLaw LLP

(57) ABSTRACT

The invention relates to a device (1) for the treatment of a biological fluid, comprising at least three chambers, wherein a first chamber (3), which is provided for receiving the biological fluid, and a second chamber (7), which is provided for receiving a gas, are separated from each other by at least one gas-permeable and liquid-impermeable membrane (9), said membrane (9) being used to transfer gas molecules between the first and second chambers (3, 7), and wherein the first chamber (3) and a third chamber (13) are separated from each other by at least one liquid-permeable membrane (15) which is used to transfer one or more components between the first and third chambers (3, 13). The second chamber (7) is delimited or enclosed by the at least one gas-permeable and liquid-impermeable membrane (9) and is located inside the first chamber (3) or is substantially enclosed by the first chamber (3) such that the biological fluid surrounds the second chamber (7). Similarly, the third chamber (13) is delimited or enclosed by the at least one liquid-permeable membrane (15) and is located inside the first chamber (3) or is substantially enclosed by the first chamber (3) such that the biological fluid surrounds the third chamber (13).

21 Claims, 5 Drawing Sheets

(51) Int. Cl.
    *C12M 1/36*     (2006.01)
    *C12M 1/38*     (2006.01)
    *B01D 63/02*     (2006.01)
    *A61M 1/16*     (2006.01)
    *A61M 1/34*     (2006.01)
    *B01D 63/04*     (2006.01)

(56) References Cited

U.S. PATENT DOCUMENTS

| | | |
|---|---|---|
| 3,989,626 A | 11/1976 | Bentley et al. |
| 4,111,659 A | 9/1978 | Bowley |
| 4,405,688 A | 9/1983 | Lowery et al. |
| 5,501,663 A * | 3/1996 | Hattler et al. ............ 604/26 |
| 2007/0004023 A1 * | 1/2007 | Trachtenberg ............ 435/266 |

FOREIGN PATENT DOCUMENTS

| | | |
|---|---|---|
| DE | 10017690 A1 | 10/2001 |
| DE | 102006020494 A1 | 10/2007 |
| EP | 1524000 A2 | 4/2005 |
| JP | 61-029360 A | 2/1986 |
| JP | 62-047369 A | 3/1987 |
| JP | 07-303695 A | 11/1995 |
| JP | 2006524567 A | 11/2006 |
| JP | 2007289695 A | 11/2007 |
| WO | 02076529 A1 | 10/2002 |
| WO | 2005075007 A1 | 8/2005 |
| WO | 2006057473 A1 | 6/2006 |
| WO | WO 2006057473 A1 * | 6/2006 |

* cited by examiner

DEVICE FOR THE TREATMENT OF BIOLOGICAL FLUID

RELATED APPLICATIONS

This application is filed under 35 U.S.C. §371 as the U.S. national phase of International Application PCT/EP2010/000852, filed Feb. 11, 2010, which designated the U.S. and claims priority to the German Patent Application No. 10 2009 008 601.3, filed Feb. 12, 2009. The entire disclosure of both applications, including the drawings, is hereby incorporated herein by reference.

BACKGROUND OF THE INVENTION

The invention relates to a device for the treatment of a biological fluid, particularly a device comprising a chamber which is suitable for receiving a biological fluid, and another chamber which is suitable for receiving a gas, wherein the chambers are separated from each other by a gas-permeable membrane, and wherein the membrane allows a transfer of gas molecules between the chambers.

It is a gassing or degassing device, in which one or more gases can pass from one medium into another, or a gas exchange device, which allows the exchange of one or more gases between two media. Such devices are used in the fields of chemistry, biotechnology and medicine. An important application in medicine is the enrichment of blood with oxygen and/or the removal of carbon dioxide from blood. Such measures are e.g. essential for surgery of various characters and in the treatment of various pulmonary diseases.

Currently, the only long term effective treatment option for patients with end stage functional lung disease is lung transplantation. Other medical solution to permanently replace the function of the lungs does not however exist. In patients suffering from chronic lung diseases and which are not eligible for a lung transplant, there is a need for an artificial lung-assist. An example of this is premature infants who typically need support for their lung function over several weeks or even months. There is also a need for lung-assist devices for patients awaiting lung transplantation.

Patients who must be treated with artificial lung-assist procedure often also suffer from additional renal insufficiency. Diseases that can lead to lung failure, may require large volumes of fluid resuscitation, and patients often receive significant amounts of blood products. The resulting physical overload with fluids may possibly lead to a general deterioration of the patient's condition, to pulmonary oedema or even complete organ failure. Such patients are therefore connected to an additional hemodialysis or hemofiltration device. This leads however to a complicated constellation of treatment devices and greater stress on the vascular system of the patient.

BRIEF DESCRIPTION OF THE INVENTION

The object of the present invention is to provide an improved device for treating a biological fluid, which can be used in the fields of chemistry, biotechnology and medicine, and can particularly be used for gassing or degassing or for gas exchange in the blood.

This object is solved by a device according to claim 1, claim 12 or claim 32. Preferred features of the invention are set forth in the dependent claims.

The invention provides a device for the treatment of a biological fluid comprising at least three chambers, wherein a first chamber which is suitable for receiving the biological fluid, and a second chamber which is suitable for receiving a gas, are separated from each other by at least one gas-permeable and fluid-impermeable membrane, which membrane serves for the transfer of gas molecules between the first and second chambers, and wherein the first chamber and a third chamber are separated from each other by at least one liquid-permeable membrane, which serves for a transfer of one or more components between the first and third chambers.

The respective membranes are typically semi-permeable, and typically have defined pores, the size of which determines the function and the effects of each membrane. In other words, any membrane may on the one hand be a porous membrane, that is to say, a membrane that comprises discrete pores. On the other hand, the membrane can be a homogeneous solubility membrane without discrete pores, in which the material transport is ensured by dissolution of the permeate (e.g. the gas) in the polymer, and the separation takes place due to different solubilities in the polymer. Preferably, the membrane is a non-porous permeable membrane. The gas exchange may be subject to the convective and diffusive mass transfer/exchange. Preferably, the gas exchange is by diffusion and is determined by the difference of gas concentration on both sides of the membrane.

In a preferred embodiment of the invention, the first chamber is designed as a flow chamber and has an inlet and an outlet. Preferably, at least one of the second and third chambers is also designed as a flow chamber. The first chamber is preferably intended and suitable for a flow in a direction opposite or transversely to the flow direction of the second or third chamber.

In a preferred embodiment of the invention, the second chamber is separated from or surrounded by the at least one gas-permeable and liquid-impermeable membrane. Similarly, the third chamber is preferably separated from or surrounded by the at least one liquid-permeable membrane.

The membranes between the respective chambers form separating or contact surfaces at which the transfer or passage of the molecules or components from one chamber into another takes place. At the at least one gas-permeable and liquid-impermeable membrane between the first and second chambers e.g. a gassing and/or degassing of the biological fluid can be performed. Furthermore, at the at least one liquid-permeable membrane that separates the first and third chambers from each other, an additional treatment of the biological fluid can be carried out. Since the first chamber intended for the biological fluid has a membranous separation or contact surface with both the second chamber and the third chamber, with the device of the invention two different treatments of the biological fluid can be carried out simultaneously. In other words, the inventive device provides a structure that allows multiple simultaneous treatments of the biological fluid. According to the invention, at least one and preferably each of the chambers are at least partially formed of the respective membrane or membrane structure. In a preferred embodiment of the invention, each of the second and third chambers is at least partially and preferably completely separated from or surrounded by the respective membrane.

In a preferred embodiment of the invention, the second chamber is located in or within the first chamber, i.e. the second chamber is substantially surrounded by the first chamber. Similarly, the third chamber is preferably located in or within the first chamber, such that the third chamber is also substantially surrounded by the first chamber. By arranging the second and third chambers within and substantially surrounded by the first chamber, the separating surface between the respective chambers can be maximized Thus, the entire surrounding surface of the respective chambers formed by the membrane can serve for the transfer or passage of molecules or components between the biological fluid contained in the first chamber and the second and third chambers.

If the second and third chambers are disposed within the first chamber, the biological fluid flows on the outside of the second and third chambers and around them. As a result, the dimensions of the first chamber can be made relatively large so that the biological fluid has not to be pressed over long distances through a narrow gap or channel. By that means, high pressure drops in the first chamber can be avoided. Furthermore, when the first chamber is intended and suitable for the biological fluid flow in a direction transversely to the second and third chamber, the second and third chambers within the first chamber can act as a static mixer, which may result in an improved exchange or transfer between the biological fluid and the second and third chambers.

In a preferred embodiment of the invention, the at least one gas-permeable and liquid-impermeable membrane is selectively permeable substantially for certain gases, in particular for oxygen and/or carbon dioxide. This embodiment is particularly suitable for gassing of biological fluid (e.g. blood) with oxygen (in a so-called oxygenator) and/or degassing of the biological fluid (e.g. blood) of carbon dioxide (in a so-called ventilator). In other words, this membrane is particularly suitable for an exchange of oxygen from the second chamber into the blood contained in the first chamber. At the same time, this membrane can support or allow the removal of carbon dioxide from the blood into the second chamber. The at least one gas-permeable and liquid-impermeable membrane may also be not or only slightly permeable to nitrogen.

In one embodiment of the invention, the third chamber is suitable for a negative pressure with respect to the first chamber to support or promote a transfer of liquid components from the biological fluid into the third chamber. The at least one liquid-permeable membrane between the first and third chambers is preferably suitable for a filtration procedure, in particular a hemofiltration procedure. In such a case, the membrane is selected such that certain components or fractions of the biological fluid are transferable through the membrane and others are not. In other words, the fluid-permeable membrane located between the first and third chambers should be determined and selected according to the desired treatment of the biological fluid.

In a hemofiltration procedure, e.g. serum (i.e. mainly water) is squeezed off from the blood through the membrane, and larger molecules such as proteins and blood cells are retained. The third chamber may be connected to a pump or an exhaust device to create a negative pressure. Alternatively or additionally, the biological fluid in the first chamber could be (e.g. lightly) pressurized to support the required transport of the component (e.g. water) from the biological fluid into the third chamber.

In another embodiment of the invention, the third chamber is suitable for receiving a liquid to support or promote a transfer of the component(s) from the biological fluid into the third chamber. The at least one liquid-permeable membrane located between the first and third chambers is preferably suitable for a dialysis procedure, especially a hemodialysis procedure. In that case, the third chamber is preferably suitable for the uptake of a dialysis solution. Here, the principle of concentration equalization of small molecular substances of two liquids, which are separated by the liquid-permeable, semi-permeable membrane (osmosis) is used. Separated by the membrane, there is on one side the blood including nephrotoxins, electrolytes such as potassium and phosphate, as well as urinary excreted substances. On the other side of the membrane, there is a germ-free solution, the water of which having been treated by reverse osmosis, and which contains no waste products but has an electrolyte content according to the specific needs of the patient. The semi-permeable membrane between blood and dialysis solution has pores which allow to pass small molecules such as water, electrolytes and urinary excreted substances (e.g., urea, uric acid), but retain large molecules such as proteins and blood cells.

It lies within the discretion of the skilled person to select a membrane material having the appropriate specific permeability for a particular gas or for specific molecules for the intended use of the inventive device. Permeability factors for many membrane materials are known in the art. The gas-permeable and liquid-impermeable membrane used in the device of the invention can for example be made of any materials available, which have good gas permeability. Good gas permeabilities for example, is given at values above 100 $ml/m^2$, preferably above 1,000, more preferably above 5,000, more preferably above 10,000 and most preferably above 20,000 $ml/m^2$ per hour at 24 atm (i.e. above 20,000 $ml/m^2$ within 24 hours of each bar pressure difference), and at 25° C., 90% relative humidity (RH) and a material thickness of about 50 µm, depending on the desired purpose with respect to the specific desired gas (for example, in particular, oxygen or carbon dioxide). Furthermore, the membrane is substantially impermeable to liquid, i.e. it has a moisture permeability of <1.000, preferably <500, more preferably <100 and even more preferably <10 $g/m^2$ (i.e. $gH_2O/m^2$) in 24 h, 40° C., 90% RH.

According to the invention, the membrane can be made of or comprise an organic or inorganic material. Inorganic membrane materials include glass, ceramics (e.g. alumina, titanium dioxide or zirconium oxide), metal, silicon or carbon. Organic membrane materials include, in particular, polymer materials such as polyacrylamides, polyacrylonitriles, polyamides, polybenzimidazoles, polybutadiene, polycarbonate, polydimethylsiloxanes, polyether sulfones, polyether imides, polyolefines, polyethylene terephthalates, polymethylmethacrylate, polymethyl pentene, polyphenylene oxide, polystyrene, polysulfones, polyvinyl alcohol, polyvinyl chloride, polyvinylidene fluoride, other halogenated hydrocarbons, and cellulose, and cyclic olefin copolymers (COC). In a preferred embodiment of the invention, at least one of the membranes consists of or comprises an organic material, wherein the organic material preferably is or comprises a polymer, a polymer composite (i.e. a mixture of different polymers or copolymers) or a polymer layer (i.e. polymer laminates).

The material of the at least one gas-permeable and liquid-impermeable membrane is preferably a polyolefin, more preferably polymethylpentene (PMP). The material of the at least one liquid-permeable membrane can also be a polyolefin, although polyethersulfone (PES) is preferred. The membranes have a wall thickness ranging for example from 10 µm to 200 µm, and preferably in the range of 20 µm to 100 µm. Preferably, the membranes have a suitable support material for stabilization. In a preferred example, at least one of the membranes, and preferably all of the membranes are stabilized by a support material. Preferably, the membrane comprises a stabilizing support layer selected from the group consisting of porous foams, ceramics, polymers, if necessary, a support layer of TPX. The membranes can also be provided with an outer skin or layer in the range of 0.1 µm to 1 µm, for example, with a diffusive layer.

In a preferred embodiment of the invention, the second chamber is divided into several chambers, such that the device includes a plurality of second chambers, which are suitable for receiving a gas and separated from the first chamber by a gas-permeable and liquid-impermeable membrane. The plurality of second chambers are located within the first chamber or are substantially surrounded by the first chamber. Preferably, the second chambers have an elongated and preferably substantially cylindrical structure which comprises in a cross-section one or more continuous cavities. A wall of the second chambers demarcating the cross section at least partially forms the gas-permeable and liquid-impermeable membrane.

In a particularly preferred embodiment of the invention, the plurality of second chambers are arranged in one or more rows side by side and preferably also in a distance from each other. Further, the plurality of second chambers may be arranged in several layers. The second chambers are formed, for example, as hollow bodies, preferably as hollow fibres, such that the wall of each hollow body or of each hollow fibre forms the liquid-permeable and fluid-impermeable membrane. The distance between the plurality of adjacently disposed second chambers is preferably in the range of 50 µm to 1 cm, more preferably in the range of 100 µm to 1 mm, and even more preferably in the range 100 µm to 500 µm. This distance can arbitrary be chosen or set.

Similarly, the third chamber can be divided into several chambers, such that the device includes a plurality of third chambers which are separated from the first chamber by a liquid-permeable membrane and which are suitable for removal/withdrawal of one or more components of the biological fluid. The plurality of third chambers are located within the first chamber or are substantially surrounded by the first chamber. Preferably, the third chambers have an elongated and preferably substantially cylindrical structure which comprises in a cross-section one or more continuous cavities. A wall of the third chambers demarcating the cross section at least partially forms the liquid-permeable membrane.

In a particularly preferred embodiment of the invention, the plurality of third chambers are arranged in one or more rows side by side and preferably also in a distance from each other. Furthermore, the plurality of third chambers may be preferably arranged in several layers. The third chambers are for example formed as hollow bodies, preferably as hollow fibres, such that a wall of each hollow body or each hollow fibre forms a liquid-permeable membrane. The distance between the several adjacent third chambers is preferably in the range of 50 µm to 1 cm, more preferably in the range of 100 µm to 1 mm, and even more preferably in the range of 100 µm to 500 µm. As described for the second chamber, this distance can arbitrary be chosen or set.

In a preferred embodiment of the invention, an elongated alignment of the second chamber(s) extends transversely and preferably in a right angle to an elongated alignment of the third chamber(s). If a plurality of second chambers are arranged in rows side by side and together form a layer, and if a plurality of third chambers are arranged in rows side by side and together also form a layer, these layers can be stacked on each other such that an elongated alignment of the second chambers extends transversely, and preferably in a right angle, in respect of an elongated alignment of the third chambers.

The critical components of the inventive device in terms of its durability are the membranes. The current diverse clinical applications of organ supporting systems with foreign surfaces that come into contact with blood, has shown that it can result in unwanted systemic reactions (e.g., a pro-inflammatory immune response). In the long-term use of conventional blood contact surfaces, an accumulation of plasma proteins and cells leads to a cross-sectional narrowing and thrombosis. In addition, long-term use results in the formation of a proliferative inner layer, which is referred to as "neo-intima." In particular, this phenomenon is observed in oxygenators, which are used to support lung function, for example in heart-lung machine, but also in artificial heart systems or cardiac support systems or hemodialysis devices. Therefore, the membrane should and has to be improved in various ways in its stability/durability. In an embodiment of the present invention, the membranes can be treated by plasma activation.

In a further embodiment of the invention, in particular for the use of the device for treating a biological fluid in medicine, at least one of the membranes, preferably the at least one gas-permeable and liquid-impermeable membrane, and more preferably each of the membranes, can be populated with cells, preferably epithelial cells. For a long-term applicable inventive gas transfer device in the medical context (for example as a lung support system), the colonization of the membrane with cells provides for a significant extension of durability, because a non-specific accumulation of substances from the used media on the membrane is prevented or strongly inhibited, and consequently the membrane is not or only slightly deteriorated in its gas permeability over time. In a preferred embodiment of the invention, at least one of the membranes, preferably the at least one gas-permeable and liquid-impermeable membrane, and more preferably all of the membranes (i.e. also the at least one liquid-permeable membrane) are coated with one or more substances selected from the group consisting of (poly)-saccharide, preferably heparin, nucleic acid, protein, preferably albumin For the colonization of the membrane with cells or for the coating of the membrane with other substances, it can be advantageous or even necessary to modify the surface of the membrane in advance. Procedures for modification of membranes are known in the art and may be selected by the skilled person depending on the intended application. For example, it may be necessary to alter the hydrophobicity/hydrophilicity/charge density of the membrane, for example by physical or chemical treatment of the membrane to improve the adhesion.

In a preferred embodiment of the invention, the at least one gas-permeable and fluid-impermeable membrane that separates the first and second chambers from each other, is typically structured (textured) on at least one side. Preferably, the side of the membrane facing the biological fluid in first chamber is structured. In this context, reference is made to the parallel international patent application PCT/EP2009/006403, the content of which is hereby incorporated into the present application. The beneficial properties (e.g. the reduction of flow resistance) of a structured membrane on gas transfer are especially evident in the case of liquids. The geometry of the structures on the membrane can arbitrary be varied. Thus, channels and/or ramifications can be used as structures on the membrane, which, for example, mimic the capillary structure of the natural lung.

BRIEF DESCRIPTION OF THE DRAWINGS

The invention will now be illustrated by means of specific exemplary embodiments as shown in the accompanying drawings, in which like features are given the same reference numbers.

DESCRIPTION OF THE EMBODIMENTS OF THE INVENTION

Figure 1:
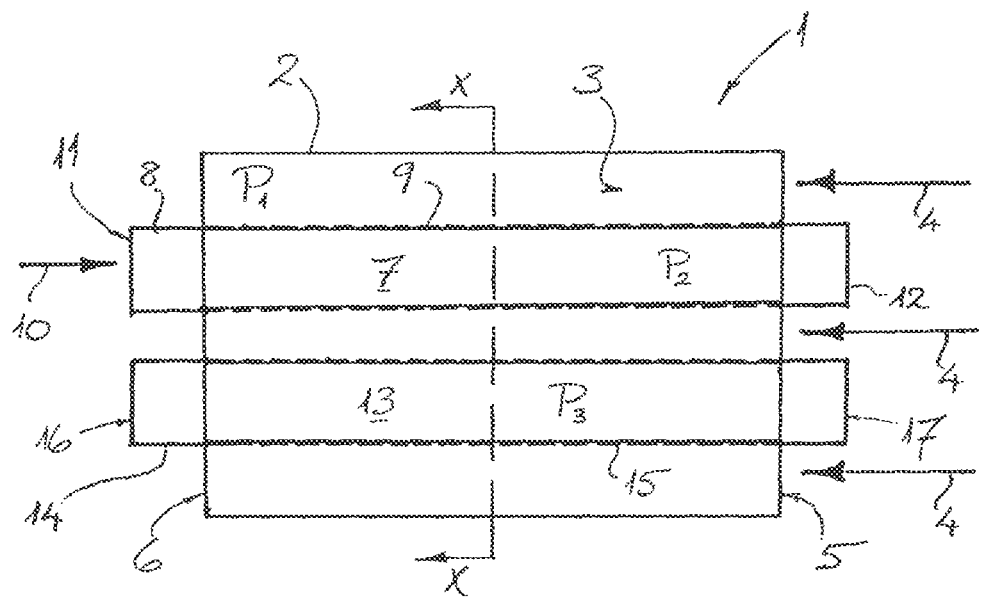
FIG. 1 is a schematic side view of a device according to a basic embodiment of the invention.
Figure 2:
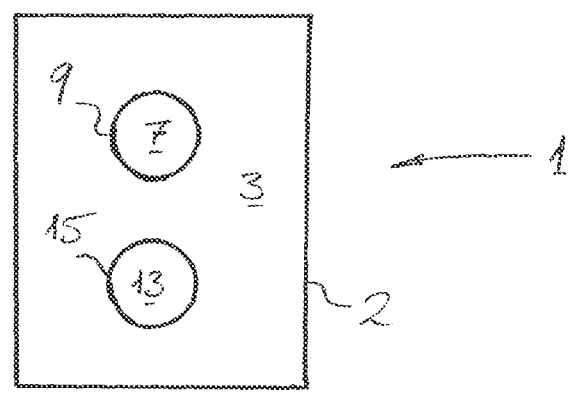
FIG. 2 is a schematic cross-section in direction X-X of the device according to the basic embodiment of the invention of FIG. 1.

In FIGS. 1 and 2 a simple representative example of the inventive concept is shown. A device 1 according to the invention includes a housing 2 which encloses or partially defines a first chamber 3. The first chamber 3 is suitable for receiving a biological fluid (as e.g. blood) and is designed as a flow chamber. The biological fluid or blood flows in the direction indicated by the arrows 4 through an inlet 5 in the housing 2 into the first chamber 3 and leaves the first chamber 3 through an opposite outlet 6. The housing 2 is preferably made of a plastic, which does not chemically react with the biological fluid, such as polyethylene or polyurethane.

Furthermore, the device 1 has a tubular second chamber 7 which extends throughout the first chamber 3 and is substantially surrounded by the first chamber 3. A tubular wall 8 enclosing the cavity of the second chamber 7 is relatively thin and is preferably made of a plastic. The wall 8 serves as a support material for an outer layer, which together with the wall 8 forms a gas-permeable and liquid-impermeable membrane 9, such that the tubular wall 8 allows a transfer of gas molecules between the first chamber 3 and the second chamber 7. In other words, the membrane 9 forms a separating or contact surface at which an intimate contact between the molecular components of the blood and the medium contained in the second chamber can be accomplished or take place.

The second chamber 7 is suitable for receiving a gas such as oxygen and is also designed as a flow chamber. The gas-permeable and liquid-impermeable membrane 9 is preferably selectively permeable to oxygen and carbon dioxide. The oxygen flows in the direction shown by arrow 10 through an inlet 11 into the second chamber 7 and leaves the second chamber 7 through an opposite outlet 12. The oxygen that flows through the second chamber 7 is however also partly transferred through the gas-permeable and liquid-impermeable membrane 9 into the blood flowing through the first chamber 3. In this manner, an enrichment of the blood with oxygen is accomplished. In a similar way, a transfer or removal of carbon dioxide from the blood through the membrane 9 into the second chamber 7 can be accomplished, such that a so-called ventilation or lung-assist procedure takes place at the membrane 9.

The pressure $P_1$ and/or the flow of biological fluid or blood in the first chamber 3 in relation to the pressure $P_2$ and/or to the flow of oxygen flowing through the second chamber 7 can be selected or adjusted such that a desired transfer of oxygen into the blood and/or of carbon dioxide from the blood is achieved. The blood can be transported through the first chamber 1 by means of e.g. a pump (not shown), or it may flow through the first chamber 1 only under the pressure of the circulatory system of the patient.

Referring again to FIGS. 1 and 2, the device 1 also includes a tubular third chamber 13, which extends as the second chamber through the first chamber 3 and is substantially surrounded by the first chamber 3. A tubular wall 14 that surrounds the cavity of the third chamber 13 is relatively thin and is preferably made of a plastic. As to the second chamber 7, the wall 14 serves as support material for an outer layer, which together with the wall 14 forms a membrane 15, which is however in this case liquid-permeable, such that the tubular wall 14 permits a transfer of liquid components between the first chamber 3 and the third chamber 13. In particular, this membrane 15 forms a separation or contact surface, which serves for removal/withdrawal of one or more liquid components of the biological fluid.

In a particular embodiment, the third chamber 13 is suitable for a connection to a suction device (not shown) in order to create a slight negative pressure in the third chamber 13 (relative to the first chamber 3). This vacuum supports or promotes a transfer of liquid components such as water from the blood flowing through the first chamber 3 into the third chamber 13. In such a way, the fluid-permeable membrane 15 located between the first and third chambers, functions as a filter via which smaller molecules like water are squeezed off from the blood and larger molecules such as proteins and blood cells are retained.

In an alternative embodiment, the third chamber 13 is suitable for receiving a dialysis solution, to promote a transfer of the component(s) from the biological fluid into the third chamber. As such, the third chamber 13 may also be designed as a flow chamber, wherein the dialysis solution is transported under the influence of a pump (not shown) from an inlet 16 through the third chamber 13 to an outlet 17 in a counter flow relative to the blood. As already mentioned above, here, the principle of concentration equalization of small molecular substances of two liquids, which are separated by the liquid-permeable, semi-permeable membrane (osmosis) is applied. The semi-permeable membrane 15 between the blood and the dialysis solution has pores, which allow to pass small molecules such as water, electrolytes and urinary excreted substances (e.g., urea, uric acid) but hold back large molecules such as proteins and blood cells.

The inventive device 1 has a structure that allows multiple simultaneous treatments of the biological fluid (in this case blood). Firstly, the blood can be treated with an enrichment of oxygen or a removal of carbon dioxide. Secondly, the blood can be treated simultaneously by means of a filtration or dialysis procedure. Thus, the invention provides a device which enables a simpler and more efficient treatment of a patient suffering from a pulmonary and renal insufficiency. Furthermore, because the second and third chambers are disposed within and substantially surrounded by the first chamber, the device 1 has a structure that maximizes the separation or contact surface of the biological fluid with the respective chambers. The entire surrounding surface of the respective second and third chambers formed by the membrane thereby serves for the transfer or passage of molecules or components between the biological fluid contained in the first chamber and the media contained in the second and third chambers.

Figure 3:
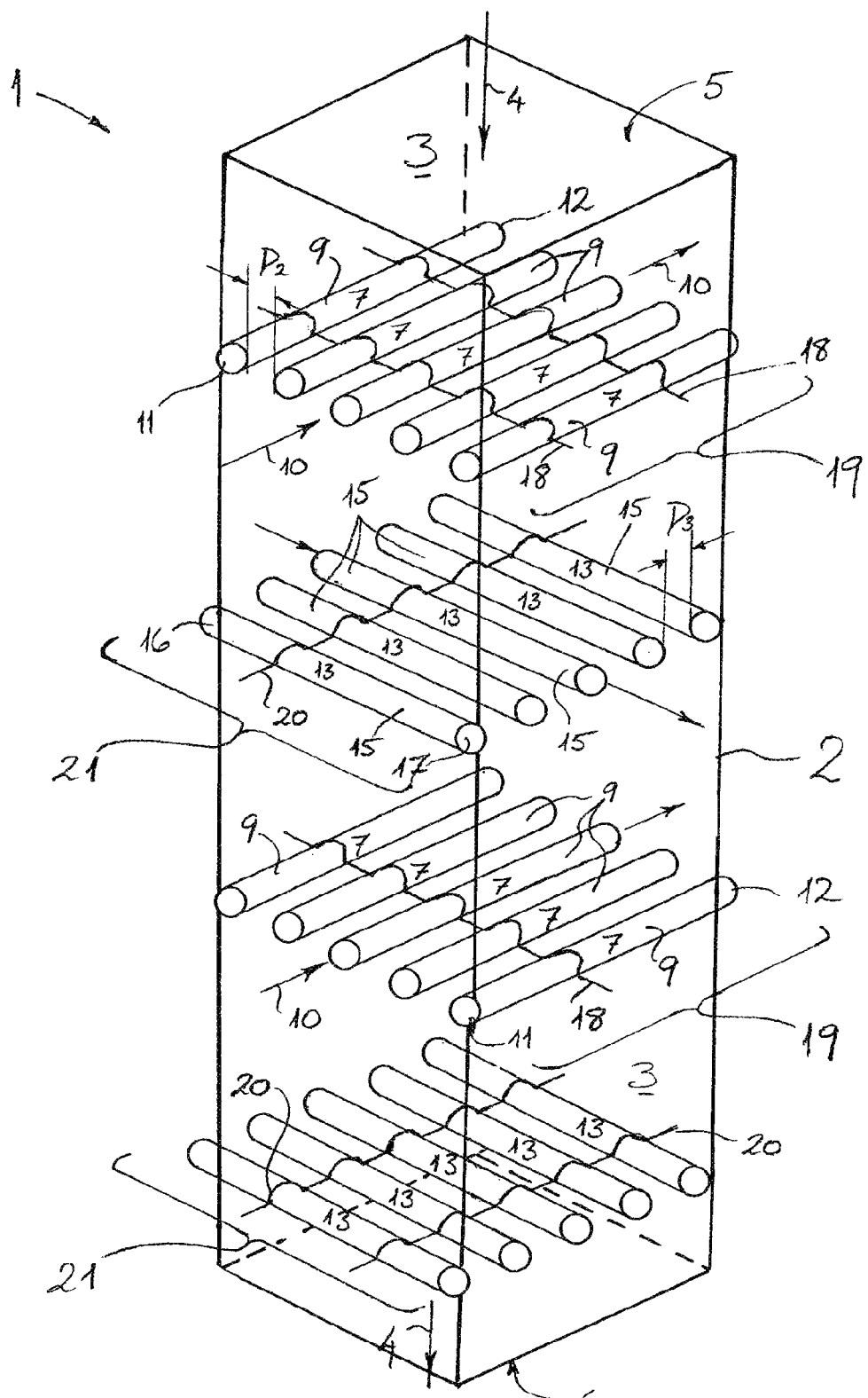
FIG. 3 is a schematic isometric view of a device according to a preferred embodiment of the invention.

With reference to FIG. 3, a particularly preferred embodiment of the invention will now be explained. The schematic diagram in FIG. 3 shows an inventive device 1 having a housing 2. As in the first exemplary embodiment, the housing 2 encloses or defines (at least partially) a first chamber 3. The first chamber 3 is suitable for receiving a biological fluid (such as e.g. blood) and is designed as a flow chamber. The biological fluid or blood flows in the direction shown by arrow 4 through an inlet 5 in the housing 2 into the first chamber 3 and leaves the first chamber 3 through an opposite outlet 6. As before, the housing 2 is preferably made of a plastic such as polyethylene or polyurethane.

The device 1 in FIG. 3 has a plurality of tubular second chambers 7, which are arranged side by side in rows. The second chambers 7 extend in parallel throughout the first chamber 3 and are substantially surrounded by the first chamber 3. In this embodiment, the tubular walls 8, which surround the cavities of the second chambers 7, are in the form of hollow fibres made of polymethylpentene (PMP, also known as TPX), e.g. foamed TPX. These walls 8 and their outer surfaces or layers form gas-permeable and fluid-impermeable membranes 9 allowing a transfer of gas molecules between the first chamber 3 and the second chambers 7 located within the hollow fibres. The membranes 9 again form separating or contact surfaces at which an intimate contact between the molecular components of the blood and the medium contained in the second chambers can be accomplished or take place.

The second chambers 7 are suitable for receiving a gas such as oxygen and also designed as flow chambers. The gas-permeable and fluid-impermeable membranes 9 are selectively permeable to oxygen and carbon dioxide. The oxygen flows through inlets 11 in a direction as shown by the arrow 10, into the second chamber 7 and leaves the second chamber 7 through opposing outlets 12. As before, a portion of the oxygen flowing through the second chamber 7 passes via the gas-permeable and liquid-impermeable membranes 9 into the blood flowing through the first chamber 3, which leads to an enrichment of the blood with oxygen. In a similar way, a transfer or removal of carbon dioxide from the blood via the membranes 9 in the second chamber 7 takes place, such that a so-called ventilation or lung-assist procedure occurs.

The TPX fibres which are arranged in a row/plane side by side and form the second chambers 7 are interconnected with warp threads 18 in a textile technical procedure. This creates a kind of fibre mat 19 with defined distances $D_2$ between the fibres. This distance $D_2$ between the fibres serves to ensure that the blood flowing through the first chamber 3 can flow through the mat 19 and thus can come into a maximum contact with the contact surfaces of the membranes 9. In this embodiment, the individual TPX hollow fibres have an outer diameter ranging from 100 μm to 1 mm, preferably in the range of 200 μm to 600 μm (e.g. an outer diameter of about 400 μm with a wall thickness of about 100 μm), and they are arranged in each row or layer side by side with a distance $D_2$ in the range of 100 μm to 500 μm. This distance can be chosen arbitrarily. Therefore, it is clear that a variety of TPX fibres can be laid side by side and processed into mats 19. The dimensions of the TPX hollow fibres membrane mat 19 are, for example, about 10 cm×15 cm.

After the TPX hollow fibres are processed into mats 19, the mats 19 can then be further processed by stacking them one upon the other. In FIG. 3, only two layers or mats 19 of the second, parallel extending chambers 7 are shown, and these are stacked one upon the other. However, it is understood by the skilled person that a multitude of those mats 19 can be provided one upon the other within the first chamber 3. Although not shown in FIG. 3, the ends of the TPX fibres forming the second chambers 7 are bundled together or interconnected, such that the individual inlets 11 can be supplied with gas or oxygen from a common supply, and such that the individual outlets 12 pass in a common outlet. Preferably, this applies not only to the second chambers 7 of the individual mats 19, but for all second chambers 7 in all mats 19. This so-called "interconnection" of the fibres of the same orientation is preferably via a casting or socketing procedure, for example with polyurethane. Here in the outer region of the fibre stack, the ends of the fibres are cast round with liquid plastic. After curing of the plastic, it is cut off from the outside, slice by slice, until the interior of the fibres is opened. Thus a common supply to the individual fibres or chambers is obtained.

In addition, the device 1 in FIG. 3 has a plurality of tubular third chambers 13, which, like the second chambers 7 extend in parallel throughout the first chamber 3 and which are substantially surrounded by the first chamber 3. In this embodiment, the tubular walls 14 that enclose the cavities of the third chambers 13 are in the form of hollow fibres made of polyethersulfone (PES). The walls 14 of the hollow fibres with their outer surfaces form liquid-permeable membranes 15, which enable a transfer of fluid components between the first chamber 3 and the third chambers 13 located inside the hollow fibres. In particular, the membranes 15 form separating or contact surfaces, which serve for a removal/withdrawal of one or more components of the biological fluid.

As for the TPX-fibres, the PES-fibres which are arranged in a row or plane side by side and form the third chambers 13, are interconnected in a textile technical process by warp threads 20. This creates a kind of fibre mat 21 with defined distances $D_3$ between the PES-fibres. This distance $D_3$ between the PES-fibres may also serve to ensure that the blood flowing through the first chamber 3 can flow throughout the mat 21 and thus can achieve a maximum contact with the contact surfaces of the membranes 15. In FIG. 3 only two layers or mats 21 of third chambers 13 are shown, and these are shown as stacked layers 21. As with the second chambers 7, the individual PES-fibres in this embodiment have an outer diameter ranging from 100 μm to 1 mm, preferably in the range from 200 μm to 600 μm (e.g. an outer diameter of about 500 μm with a wall thickness of about 100 μm), and they are arranged in each row or plane side by side with a distance $D_3$ in a range of 100 μm to 500 μm. A multitude of PES-fibres can therefore be placed side by side and processed into mats 21. The dimensions of each PES-fibre membrane mat 21 also amounts to about 10 cm×15 cm. Preferably, the liquid-permeable membranes have a pore size ≤1 μm, and more preferably ≤0.5 μm (e.g., the maximum pore size is 0.5 μm). Preferably, these membranes generate a transmembrane flow of >35 ml/min.cm².bar].

After the PES-hollow fibres are made into mats 21, the mats 21 can then be further processed by stacking them one upon the other. In FIG. 3, only two layers or mats 21 of the third, parallel extending chambers 13 are shown. It will, however, understood by the person skilled in the art that a multitude of such mats 21 can be provided one upon the other in the first chamber 3.

The ends of the PES-fibres forming the third chambers 13 are bundled together or interconnected, such that the individual inlets 16 together can be applied with a negative pressure, or can be supplied with a dialysis solution via a common supply, such that the individual outlets 17 pass into a common drain. This so-called "interconnection" of the fibres of the same orientation, preferably is via a casting or socketing procedure with e.g. polyurethane, as described in connection with the second chamber 7. This applies not only to the third chambers 13 of the individual mats 21 but for all third chambers 13 within the stacked mats 21.

The elongated alignment of the parallel arranged second chambers 7 extends I a right angle to the longitudinal alignment of the parallel arranged third chambers 13, and the layers, respectively mats 19, 21 of the TPX- and PES-fibres are stacked in this example alternately and directly on or upon each other in a relatively compact arrangement. The mats 19, 21 are preferably directly placed upon each other, such that they are in contact with each other. In FIG. 3, the layers or mats 19, 21 are shown in a wide distance from each other in an "exploded" view to simplify the illustration the invention. The square arrangement of the hollow fibres and layers or mats 19, 21 in the inventive device 1 is particularly suitable for the connections to the respective second and third chambers 7, 13 (i.e. for the respective supply and discharge connection). In other words, the device 1 may be provided with a supply connection and a discharge connection for the second chambers 7 at opposite sides of the square housing 2, but also with a supply connection and a discharge connection for the third chambers 13 at the other opposite sides of the housing 2. Moreover, the housing 2 may also allow a cross-flow of the biological fluid throughout the respective membrane layers or mats 19, 21, as schematically shown in FIG. 3.

The purpose of the foregoing description is to illustrate the operation of preferred embodiments of the invention and not limit the scope of the invention. Based on the foregoing explanation, a multitude of variations will be apparent to a person skilled in the art which are covered by the disclosure of the present invention. As the skilled person will understand, for example, the above-described hollow fibre mats 19, 21 do not always have to be stacked alternately. The respective matt types 19, 21 can, for example stacked and combined in analogous groups, and these groups can then be later combined with each other. As the skilled person will also understand, the device 1 of the invention is not limited to a maximum of two treatments of the biological fluid. Rather, the construction of the inventive device 1 allows a plurality of possible simultaneous treatments.

Experimental Results in Animal Tests

In a pilot experiment using four experimental animals (pigs), an inventive device in accordance with the embodiment described in FIG. 3 was connected to each animal for the treatment of blood by means of a gas exchange ($O_2$ and $CO_2$) and hemofiltration and operated over a period of 6 hours. The inventive devices were in the form of test modules or prototypes, and the respiration, blood pressure and flow through the test module for each animal was permanently controlled. At intervals of 30 minutes, blood samples were taken for serum and blood gas analysis. The animals were artificial respirated over a period of 6 hours with the test modules (i.e., the prototypes).

Figure 4:
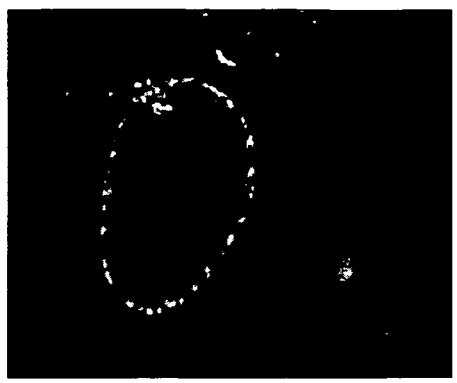
FIG. 4 shows a DAPI staining of a populated hollow fibre.

To carry out the animal experiments, two of the four modules (namely, for the animals 2 and 4) had been populated with cells. For this, A549 cells had been taken into culture and expanded over several weeks in a culture lab. After reaching the required number of cells, the cells were detached by trypsin treatment, taken into 40 ml medium and injected into the PES-fibres of the prototypes. After an incubation period of 2-3 days, the cells were adhered inside the fibres. This was demonstrated by nuclear staining of cryotome slices of fibres with the DAPI dye, as shown in FIG. 4. Blood flow through populated and non-populated modules was comparable to 1.1 vs. 1.3 liters of blood per minute, the colonization respectively pre-incubation of the prototypes had no significant effect on blood flow rates.

Figure 5:
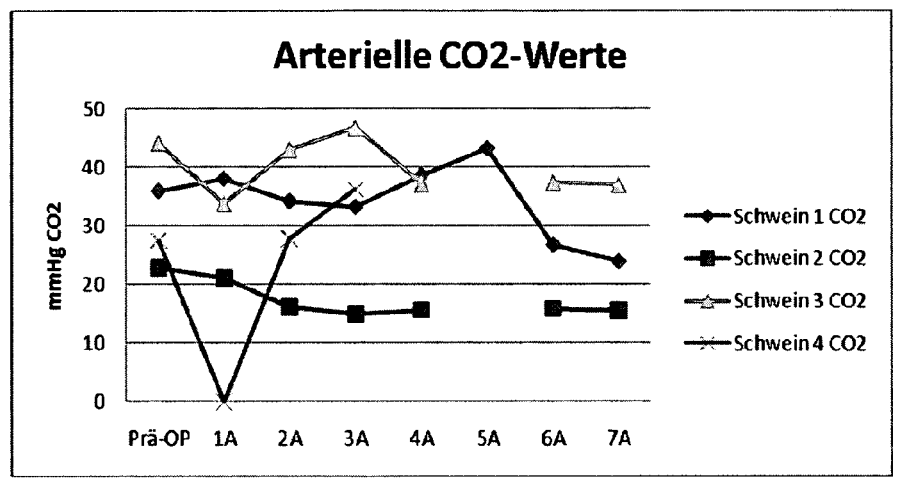
FIG. 5 shows the arterial $CO_2$ levels of four experimental animals.
Figure 6:
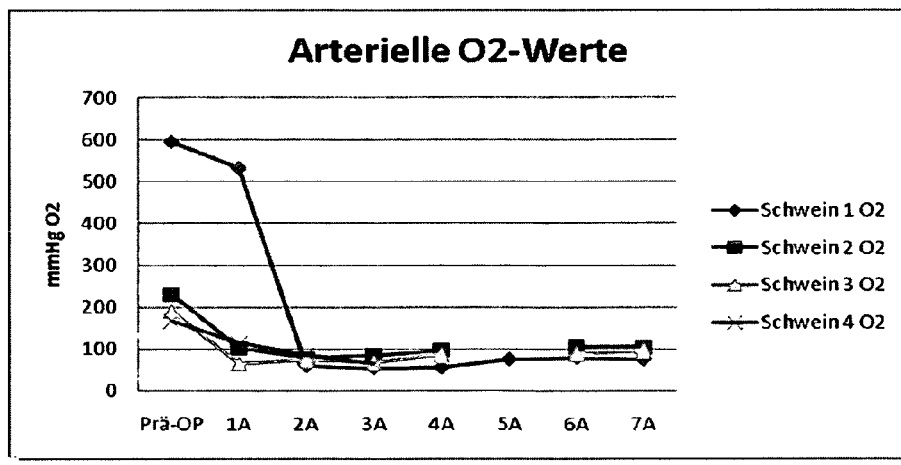
FIG. 6 shows the arterial $O_2$ levels of the four experimental animals.

As can be seen from the FIGS. 5 and 6, the arterial blood gas values for $CO_2$ (FIGS. 5) and $O_2$ (FIG. 6) show a fairly constant level over the experimental time period. In pig 2, the $CO_2$ level dropped within the first three measurements of from about 22 mmHg to about 15 mmHg. The arterial $O_2$ values were found in a range of 50-100 mmHg after connecting of the prototypes.

Figure 7:
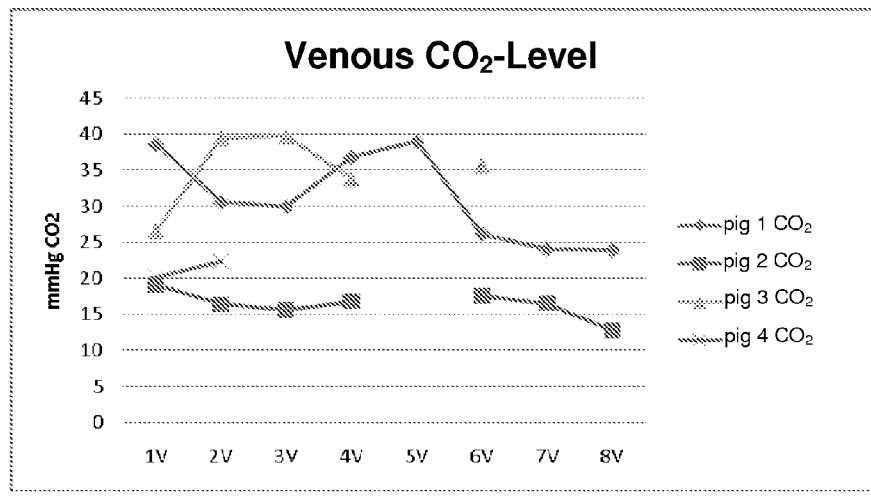
FIG. 7 shows the venous $CO_2$ levels of the four experimental animals.
Figure 8:
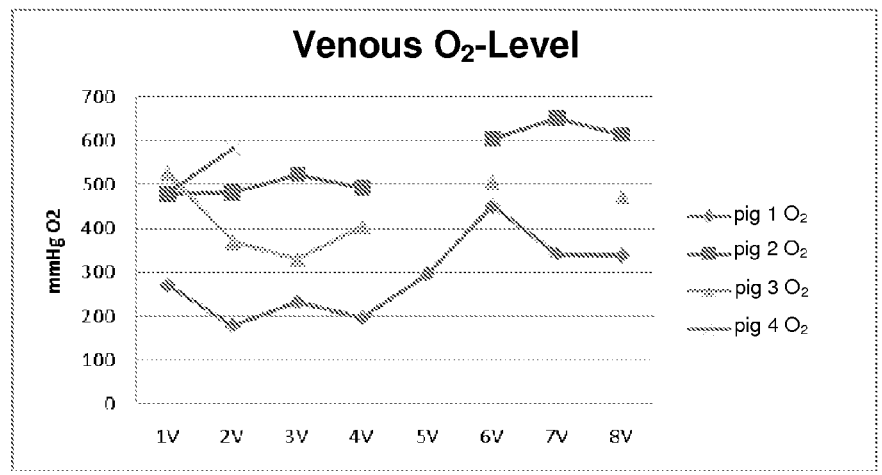
FIG. 8 shows the venous $O_2$ levels of the four experimental animals.
Figure 9:
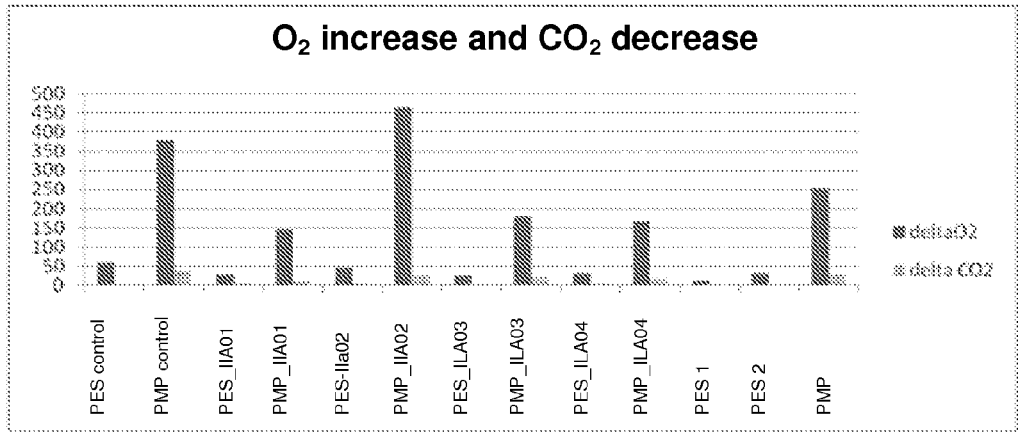
FIG. 9 shows the delta $O_2$ and $CO_2$ levels for the gas exchange performance of the inventive prototype after the animal experiment.

From the FIGS. 7 and 8, the partial pressures in the venous blood provide information about the gas transfer performance in the prototypes. It is noticeable that the venous $CO_2$ levels (FIG. 7) are only slightly lower than the arterial values. The generally low values indicate a relatively high and constant $CO_2$ elimination. The venous $O_2$ levels (FIG. 8) have a larger range. Animal 1 had the lowest $O_2$ partial pressures (200-330 mmHg), while the pigs 2 and 4 had relatively high $O_2$ partial pressures of more than 500 mm Hg. This shows the higher gas transfer performance of the populated test modules, wherein both the cellularization and the pre-incubation in serum-containing medium can have an effect on the improved gas transfer performance. In FIG. 9, the marked increase of $O_2$ in the blood via the (second) PMP-membranes of each module is shown (indicated as 01 to 04).

Because of the vascular pressures, it could be observed that serum passed through the PES membranes into the third chambers 13, i.e. into the lumen side of the hollow fibres 14. In this way, it could be shown that the fibres are permeable to plasma, and that cells on the lumen side can be supplied. In pig 3, a slightly higher pressure drop across the module as in pig 1 was observed, although both values were at a very low levels. Therefore, the pressure drops across the modules were in a very acceptable range.

Figure 10:
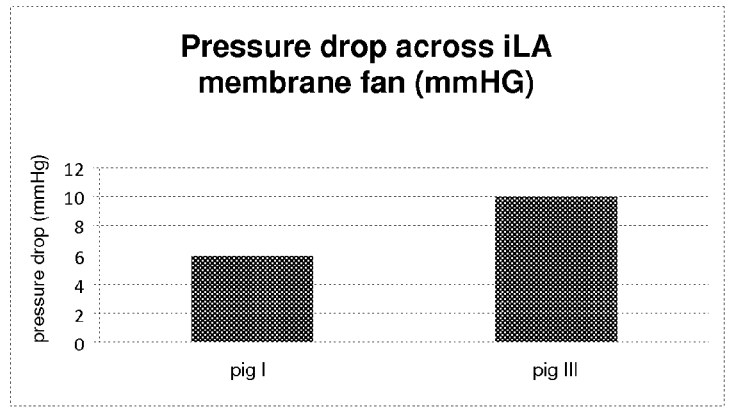
FIG. 10 shows the average pressure drop across a test module according to the invention.
Figure 11:
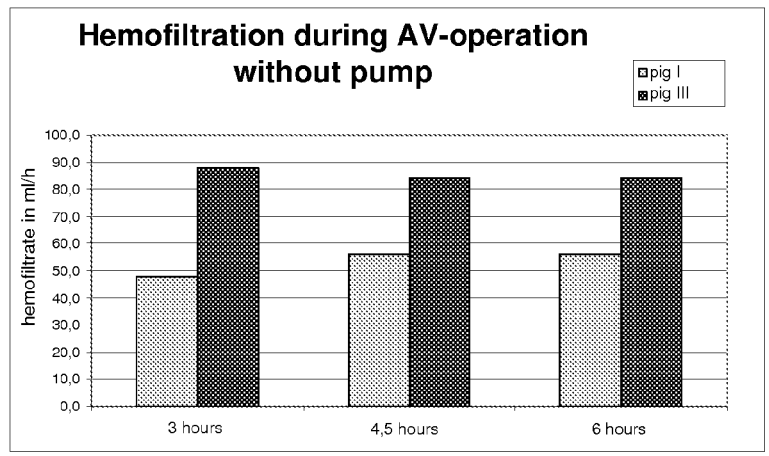
FIG. 11 shows the hemofiltrate volume for animal 1 and animal 3 from the non-populated inventive test modules.

Referring to FIG. 10, the performance of hemofiltration of the PES-fibre (through the membranes 15 in the third chambers 13) showed constant values over the entire period of 6 hours. With reference to FIG. 11, it was however remarkable that inter-individual differences (here between the modules for animal 1 and animal 3) were relatively high. This is one the one hand due to a different vascular pressure, as well as to the hemostatic situation and the fluid condition (status) of the animals.

Figure 12:
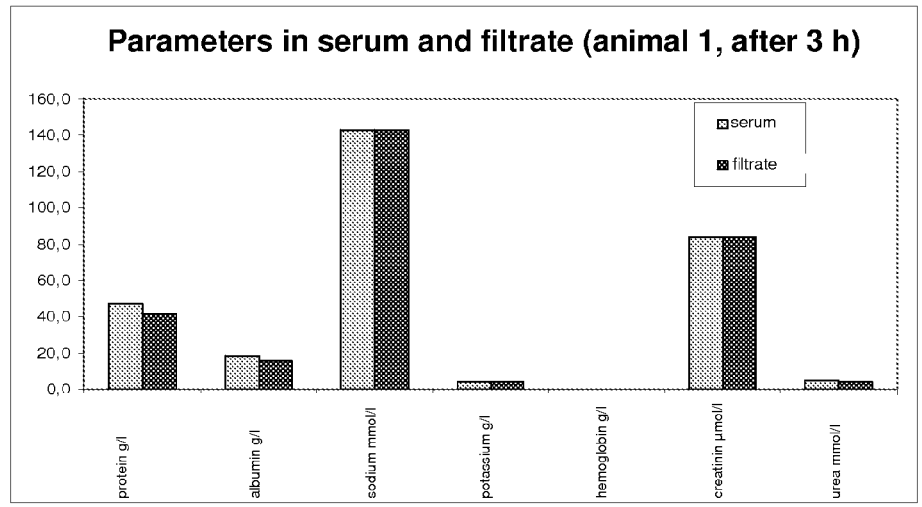
FIG. 12 shows a comparison of serum and hemofiltrate parameters.

As can be seen in FIG. 12, in animal 1 the parameters of the filtrate are only slightly different from the serum parameters. Thus, a very good performance of hemofiltration can be assumed.

What is claimed is:

1. A device for the treatment of a biological fluid, comprising
   a first chamber, which is suitable for receiving the biological fluid,
   a first mat comprising a plurality of second fibers, which are suitable for receiving a gas, wherein the first chamber and the plurality of second fibers are separated from each other by at least one gas-permeable and liquid-impermeable membrane, through which membrane gas molecules are transferable between the first chamber and the second fibers, thereby gassing and/or degassing for the treatment of the biological fluid, and
   a second mat comprising a plurality of third fibers, which are separated from the first chamber by at least one liquid-permeable membrane, and which is suitable for a removal/withdrawal of one or more liquid components of the biological fluid,
   wherein the plurality of second fibers are arranged in rows side by side forming mats of second fibers,
   wherein the plurality of third fibers are arranged in rows side by side forming mats of third fibers,
   wherein the mats of second fibers and the mats of third fibers are alternately stacked upon each other, and
   wherein an elongated alignment of the second fibers extends transversely or in a right angle to an elongated alignment of the third fibers.

2. The device of claim 1, wherein the plurality of second fibers are located within the first chamber or are substantially surrounded by the first chamber, such that the biological fluid surrounds the plurality of second chambers.

3. The device of claim 1, wherein the plurality of third fibers are located within the first chamber or are substantially surrounded by the first chamber, such that the biological fluid surrounds the plurality of third chambers.

4. The device of claim 1, wherein the plurality of third fibers are under a negative pressure relative to the first chamber to promote a transfer of the component(s) from the biological fluid into the plurality of third chambers.

5. The device of claim 1, wherein the plurality of third fibers are configured to receive a liquid to promote a transfer of the component(s) from the biological fluid into the plurality of third chambers are.

6. The device of claim 1, wherein the plurality of second fibers are divided into several chambers, such that the device comprises a plurality of second fibers which are configured to receive a gas, and which are separated from the first chamber by a gas-permeable and liquid-impermeable membrane, wherein the plurality of second fibers are located within the first chamber or are substantially surrounded by the first chamber.

7. The device of claim 1, wherein the second fibers have an elongated and substantially cylindrical structure, which comprises in a cross-section one or more continuous cavities, and that a wall of the second fibers demarcating the cross-section at least partially forms the gas-permeable and liquid-impermeable membrane.

8. The device of claim 1, wherein the plurality of third fibers are divided into several chambers, such that the device comprises a plurality of third fibers, which are separated from the first chamber by a fluid-permeable membrane and are configured to remove or withdraw one or more components of the biological fluid, wherein the plurality of third fibers are located within the first chamber or are substantially surrounded by the first chamber.

9. The device of claim 1, wherein the third fibers are connected to a pump or an exhaust device to create a negative pressure within the third fibers.

10. The device of claim 1, wherein the plurality of second fibers and third fibers are arranged horizontally in rows side by side.

11. A device for the treatment of a biological fluid, comprising
a first chamber which is suitable for receiving the biological fluid,
a first mat comprising a plurality of second fibers, which are suitable for receiving a gas, wherein each of the second fibers is demarcated or surrounded by a gas-permeable and fluid-impermeable membrane and located within the first chamber or substantially surrounded by the first chamber, such that gas molecules are transferable via the membranes between the first chamber and the second fibers, thereby gassing and/or degassing for the treatment of the biological fluid, and
a second mat comprising a plurality of third fibers, each of which is demarcated or surrounded by a fluid-permeable membrane and located within the first chamber or substantially surrounded by the first chamber, wherein the third fibers are suitable for a removal/withdrawal of one or more liquid components of the biological fluid,
wherein the plurality of second fibers are arranged in rows side by side forming mats of second fibers,
wherein the plurality of third fibers are arranged in rows side by side forming mats of third fibers,
wherein the mats of second fibers and the mats of third fibers are alternately stacked upon each other, and
wherein an elongated alignment of the second fibers extends transversely or in a right angle to an elongated alignment of the third fibers.

12. The device of claim 11, wherein the second fibers and/or the third fibers are formed as hollow bodies, or hollow fibers such that a wall of the hollow body or hollow fiber forms the respective membrane.

13. The device of claim 11, wherein the first chamber is formed as a flow chamber and designed for a flow from an inlet to an outlet in a direction opposite or transversely to the second or third fibers.

14. The device of claim 11, wherein at least one of the membranes is made of or comprises an organic material, wherein the organic material is a polymer, a polymer composite or polymer layer.

15. The device of claim 14, wherein the material of the at least one gas-permeable and liquid-impermeable membrane is a polyolefin, wherein the polyolefin is polymethylpentene; or wherein the material of the at least one liquid-permeable membrane is polyethersulfone.

16. The device of claim 11, wherein the membranes have a thickness of 10 to 100 μm.

17. The device of claim 11, wherein the second and/or third fibers has a diameter ranging from 1 μm to 1 cm.

18. The device of claim 11, wherein the at least one gas-permeable and fluid-impermeable membrane is selectively permeable for oxygen and/or carbon dioxide.

19. The device of claim 11, wherein the at least one gas-permeable and fluid-impermeable membrane is impermeable or only slightly permeable for nitrogen.

20. The device of claim 11, wherein the biological fluid is selected from the group consisting of blood, blood serum, cell suspension, cell solution and culture medium.

21. The device of claim 11, wherein the fibers are connected to a pump or an exhaust device to create a negative pressure within the third fibers.

* * * * *